United States Patent
Isono et al.

(10) Patent No.: US 7,557,233 B2
(45) Date of Patent: Jul. 7, 2009

(54) METHOD FOR SYNTHESIZING IONIC COMPLEX

(75) Inventors: Yoshimi Isono, Kawagoe (JP); Syoichi Tsujioka, Kawagoe (JP)

(73) Assignee: Central Glass Company, Limited, Ube-Shi (JP)

( * ) Notice: Subject to any disclaimer, the term of this patent is extended or adjusted under 35 U.S.C. 154(b) by 52 days.

(21) Appl. No.: 11/792,087

(22) PCT Filed: Jan. 24, 2006

(86) PCT No.: PCT/JP2006/301017

§ 371 (c)(1),
(2), (4) Date: Jun. 1, 2007

(87) PCT Pub. No.: WO2006/087889

PCT Pub. Date: Aug. 24, 2006

(65) Prior Publication Data

US 2008/0125602 A1    May 29, 2008

(30) Foreign Application Priority Data

Jan. 24, 2005 (JP) ............... 2005-015917
Sep. 5, 2005 (JP) ............... 2005-256879

(51) Int. Cl.
*C07F 9/02* (2006.01)
*C07F 5/04* (2006.01)
(52) U.S. Cl. .................. 558/84; 558/291
(58) Field of Classification Search ............ None
See application file for complete search history.

(56) References Cited

U.S. PATENT DOCUMENTS

| | | | |
|---|---|---|---|
| 6,407,232 B1 | 6/2002 | Tsujioka et al. | |
| 6,485,868 B1 | 11/2002 | Tsujioka et al. | |
| 6,506,516 B1 | 1/2003 | Wietelmann et al. | |
| 6,849,752 B2 * | 2/2005 | Tsujioka et al. | ............... 556/41 |

2002/0001755 A1    1/2002   Heider et al.

FOREIGN PATENT DOCUMENTS

| | | |
|---|---|---|
| JP | 2001-106694 A | 4/2001 |
| JP | 2001-110450 A | 4/2001 |
| JP | 2001-354681 A | 12/2001 |
| JP | 2002-519352 A | 7/2002 |

OTHER PUBLICATIONS

International Search Report dated Jun. 20, 2006 including English translation (Four (4) pages).

* cited by examiner

*Primary Examiner*—Paul A Zucker
(74) *Attorney, Agent, or Firm*—Crowell & Moring LLP

(57) ABSTRACT

A method of synthesizing an ionic metal complex corresponding to formula (1)

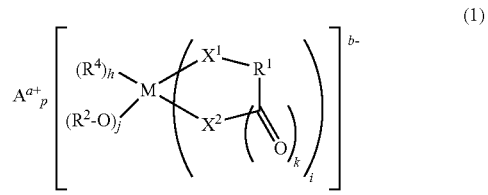

in which a compound of formula (2)

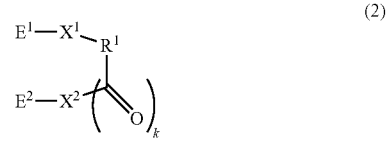

and/or a compound of formula (3)

$$E^3\text{-O}\text{—}R^2 \quad (3)$$

is reacted with a halogen containing compound in an organic solvent in the presence of a compound containing an element of group 1, group 2, group 13 or group 14 of the periodic table as a reaction aid.

6 Claims, No Drawings

METHOD FOR SYNTHESIZING IONIC COMPLEX

TECHNICAL FIELD

The present invention relates to a method for synthesizing an ionic complex, which is used as a supporting salt or additive for electrochemical devices, such as lithium cell, lithium ion cell and electric double layer capacitor, a polymerization catalyst of polyolefin and the like, or a catalyst for organic syntheses.

Hitherto, ionic complexes, such as $PF_6^-$, $BF_4^-$ and $AsF_6^-$, in which Lewis acid and F ion are combined, have been used for uses, such as supporting salt for electrochemical devices, polymerization catalyst of polyolefin and the like, or catalyst for organic syntheses, and the like, due to their characteristics of solubility, ionic dissociation property and high activity against reactions.

Under a situation that the application range has become multiple and diverse, the optimum ionic complex for each use has been searched. As its properties, there is a demand for heat resistance, hydrolysis resistance, low toxicity, recyclability, and the like. Under such situation, there have been found many complexes of a conventional manner of a simple bonding to central element. There are many synthesis methods. For example, it is possible to cite a demineralization reaction of a halide of an element corresponding to the central element and a ligand having high dissociation property, such as alkali metal, and the like. Depending on the combination of the ligand and the central element, however, the reactivity is low in some cases. There are also many cases in which a free obtainment of complex as designed is difficult (Patent Publication 1, Patent Publication 2 and Patent Publication 3).

Patent Publication 1: Japanese Patent Laid-open Publication 2002-519352

Patent Publication 2: Japanese Patent Laid-open Publication 2001-106694

Patent Publication 3: Japanese Patent Laid-open Publication 2001-354681

SUMMARY OF THE INVENTION

In view of such prior art problems, the present inventors have conducted an eager examination. As a result, we have found a method for synthesizing a novel complex, in which a reaction is conducted in organic solvent using a ligand and a halogen-containing compound as raw materials in the presence of a compound containing an element of group 1, group 2, group 13, or group 14 of the periodic table, thereby reaching the present invention.

The present invention provides a method for synthesizing an ionic metal complex having a chemical structural formula represented by the formula (1), comprising reacting at least one of a compound represented by the formula (2) and a compound represented by the formula (3) with a halogen-containing compound represented by the formula (4) or formula (5), in an organic solvent, in the presence of a compound containing an element of group 1, group 2, group 13 or group 14 of the periodic table as a reaction aid.

[Chemical Formula 1]

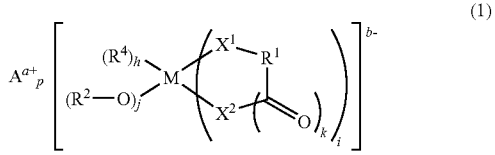

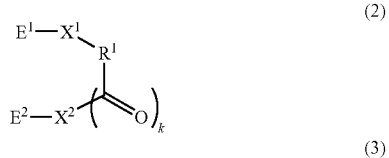

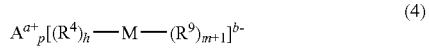

The definitions of the symbols in the formulas (1) to (5) are as follows.

M represents a transition metal or an element of group 13, group 14 or group 15 of the periodic table.

$A^{a+}$ represents a metal ion, hydrogen ion, or onium ion.

a represents 1-3, b represents 1-3, p represents b/a, h represents 1-5, i represents 0-2, j represents 0-5, k represents 0 or 1, and m represents 0-4. The total of h, i and j is 3-6. At least one of i and j must necessarily be 1 or greater.

$R^1$ represents a $C_1$-$C_{10}$ alkylene, $C_1$-$C_{10}$ halogenated alkylene, $C_3$-$C_{10}$ cycloalkylene, $C_3$-$C_{10}$ halogenated cycloalkylene, $C_6$-$C_{20}$ arylene, or $C_6$-$C_{20}$ halogenated arylene, wherein these alkylenes and arylenes may have substituents and hetero atoms in their structures, and $R^1$ existing by a number of i may bond to each other.

$R^2$ represents a $C_1$-$C_{10}$ alkyl, $C_1$-$C_{10}$ halogenated alkyl, $C_6$-$C_{20}$ aryl, $C_6$-$C_{20}$ halogenated aryl, or —C(=O)$R^3$, wherein these alkyls and aryls may have substituents and hetero atoms in their structures, and $R^2$ existing by a number of j may bond to adjacent molecules to be in a polymer form.

$R^3$ represents a halogen, $C_1$-$C_{10}$ alkyl, $C_1$-$C_{10}$ halogenated alkyl, $C_6$-$C_{20}$ aryl, or $C_6$-$C_{20}$ halogenated aryl, wherein these alkyls and aryls may have substituents and hetero atoms in their structures, and $R^3$ existing by a number of j may bond to adjacent molecules to be in a polymer form.

$R^4$ represents a halogen, $C_1$-$C_{10}$ alkyl, $C_1$-$C_{10}$ halogenated alkyl, $C_6$-$C_{20}$ aryl, $C_6$-$C_{20}$ halogenated aryl, or $X^3R^5$, wherein these alkyls and aryls may have substituents and hetero atoms in their structures, and $R^4$ existing by a number of h may bond to each other to form a ring or may bond to adjacent molecules to be in a polymer form.

$X^1$ represents O, S, $SO_3$, or $NR^6$; $X^2$ represents O, S, or $NR^7$; $X^3$ represents O, S, $SO_3$, $CO_2$, or $NR^8$.

Each of $R^5$, $R^6$, $R^7$ and $R^8$ independently represents a hydrogen, $C_1$-$C_{10}$ alkyl, $C_1$-$C_{10}$ halogenated alkyl, $C_6$-$C_{20}$ aryl, or $C_6$-$C_{20}$ halogenated aryl, wherein these alkyls and aryls may have substituents and hetero atoms in their structures, and $R^5$, $R^6$, $R^7$ and $R^8$ existing in a plural number may bond to each other through single bond or multiple bond to form a ring or may bond to adjacent molecules to be in a polymer form.

Each of $E^1$, $E^2$ and $E^3$ independently represents a hydrogen or alkali metal. Each of $R^9$ represents a halogen.

The alkyls, halogenated alkyls, aryls, and halogenated aryls used in the present invention include ones having branches and other functional groups such as hydroxy groups and ether bonds.

DETAILED DESCRIPTION

The present invention has made it possible to easily and efficiently synthesize an ionic complex, which is used as a supporting salt or additive for electrochemical devices, such as lithium cell, lithium ion cell and electric double layer capacitor, a polymerization catalyst of polyolefin and the like, or a catalyst for organic syntheses.

In the following, the present invention is described in more detail.

Herein, it suffices that an ionic complex to be synthesized, which is the target of the present invention, is one having a structure in which inorganic and organic-series ligands are bonded to the central element, and it is preferably one having a structure represented by the formula (1).

M in the formula is one selected from transition metals and elements of group 13, group 14 or group 15 of the periodic table. It is preferably Al, B, V, Ti, Si, Zr, Ge, Sn, Cu, Y, Zn, Ga, Nb, Ta, Bi, P, As, Sc, Hf, and Sb. It is more preferably Al, B or P. It is possible to use various elements as M of the center. In the case of Al, B, V, Ti, Si, Zr, Ge, Sn, Cu, Y, Zn, Ga, Nb, Ta, Sc, or Hf, the synthesis is relatively easy, too. Furthermore, in the case of Al, B or P, it has superior characteristics in terms of all aspects of low toxicity, stability and cost, as well as easiness of synthesis.

$A^{a+}$ is a metal ion, hydrogen ion, or onium ion, preferably a lithium ion, sodium ion, potassium ion, quaternary alkylammonium ion, or hydrogen ion. Specific citations of $A^{a+}$ are lithium ion, sodium ion, potassium ion, magnesium ion, calcium ion, barium ion, cesium ion, silver ion, zinc ion, copper ion, cobalt ion, iron ion, nickel ion, manganese ion, titanium ion, lead ion, chromium ion, vanadium ion, ruthenium ion, yttrium ion, lanthanoid ions, actinoid ions, tetrabutylammonium ion, tetraethylammonium ion, tetramethylammonium ion, triethylmethylammonium ion, trimethylammonium ion, triethylammonium ion, pyridinium ion, imidazolium ion, 1,3-ethylmethylimidazolium, hydrogen ion, tetraethylphosphonium ion, tetramethylphosphonium ion, tetraphenylphosphonium ion, triphenylsulfonium ion, triethylsulfonium ion, triphenylmethyl ion, and the like. In particular, in the case of the consideration of the uses of electrochemical devices and the like, lithium ion, sodium ion, potassium ion, tetraalkylammonium ions, alkyl-substituted imidazolium ions, and hydrogen ion are preferable.

The valence a of the cation $A^{a+}$ is preferably 1 to 3. If it is greater than 3, the crystal lattice energy becomes large. Therefore, there occurs a problem that dissolution in solvent becomes difficult. Therefore, it is more preferably 1 in case that high solubility is necessary. Similarly, the valence b of the anion is preferably 1 to 3, particularly more preferably 1. The constant p showing the ratio of the cation and the anion is necessarily fixed by the valence ratio b/a of both.

Next, we explain a portion of the ligand that becomes a characteristic of the ionic complex synthesized in the present invention. In the following, an organic or inorganic portion bonded to M is called a ligand.

$R^1$ in the formula (1) is one selected from a $C_1$-$C_{10}$ alkylene, $C_1$-$C_{10}$ halogenated alkylene, $C_3$-$C_{10}$ cycloalkylene, $C_3$-$C_{10}$ halogenated cycloalkylene, $C_6$-$C_{20}$ arylene, or $C_6$-$C_{20}$ halogenated arylene.

These alkylenes and arylenes may have substituents and hetero atoms in their structures. In particular, when a chelate ring is formed in conjunction with M of the center, one that forms a 5 to 10-membered ring is preferable. Being larger than 10-membered ring is not preferable, since the chelate effect becomes small.

In case that $R^1$ has hydroxy group and carboxyl group in the structure, it is also possible that this portion further bonds to M of the center. Specifically, it is possible to mention structures and the like in which, in place of hydrogen on the alkylene and the arylene, halogen, chain or ring alkyl group, halogenated alkyl group, aryl group, halogenated aryl group, alkenyl group, halogenated alkenyl group, alkoxy group, halogenated alkoxy group, aryloxy group, halogenated aryloxy group, sulfonyl group, amino group, cyano group, carbonyl group, acyl group, amide group, and hydroxy group have been introduced; and structures and the like in which, in place of carbon on the alkylene and the arylene, nitrogen, sulfur and oxygen have been introduced.

$R^1$ existing in a plural number may bond to each other. For example, it is possible to mention polyvalent ligands such as catechol, salicylic acid, and ethylenediaminetetraacetic acid. In the case of a polyvalent ligand, a chelate structure is formed in conjunction with M. Due to this chelate effect, this compound improves in heat resistance, chemical stability, and hydrolysis resistance. These ligand portions are preferably ones of electron attractive property. In particular, ones containing halogen in their structures are suitable. Ones containing fluorine are preferable.

$R^2$ is one selected from a $C_1$-$C_{10}$ alkyl, $C_1$-$C_{10}$ halogenated alkyl, $C_6$-$C_{20}$ aryl, $C_6$-$C_{20}$ halogenated aryl, or —C(=O)R$^3$. Similar to $R^1$, these alkyls and aryls may have substituents and hetero atoms in their structures, and $R^2$ existing by a number of j may bond to adjacent molecules to be in a polymer form.

$R^3$ is one selected from a halogen, $C_1$-$C_{10}$ alkyl, $C_1$-$C_{10}$ halogenated alkyl, $C_6$-$C_{20}$ aryl, or $C_6$-$C_{20}$ halogenated aryl. These alkyls and aryls may have substituents and hetero atoms in their structures, and $R^3$ existing by a plural number may bond to adjacent molecules to be in a polymer form.

$R^4$ is one selected from a halogen, $C_1$-$C_{10}$ alkyl, $C_1$-$C_{10}$ halogenated alkyl, $C_6$-$C_{20}$ aryl, $C_6$-$C_{20}$ halogenated aryl, or $X^3R^5$. These alkyls and aryls may have substituents and hetero atoms in their structures. $R^4$ existing by a number of h may bond to each other to form a ring or may bond to adjacent molecules to be in a polymer form. It is preferably an electron attractive group, particularly preferably fluorine. In case that $R^4$ is fluorine, ionic conductivity becomes very high when used as an electrolyte, due to the effects of the improvement of degree of dissociation of the ionic complex by its strong electron attractive property and of the improvement of mobility by that the size becomes small.

$X^1$ is O, S, SO$_3$, or NR$^6$. $X^2$ is O, S, or NR$^7$. $X^3$ represents O, S, SO$_3$, CO$_2$, or NR$^8$. The ligand is bonded to M through these hetero atoms. Herein, a bonding with ones other than O, S and N is not impossible, but it becomes very complicated in terms of synthesis. In case that these ligands exist by a number of 1 or greater, these ligands and M form a chelate structure, since there are bonds by $X^1$ and $X^2$ in the same ligand as a characteristic of this compound. This compound is improved by this chelate effect in heat resistance, chemical stability and hydrolysis resistance. In particular, in case that this chelate ring is a five-membered ring structure, the chelate effect is the most strongly exhibited to increase stability. Therefore, it is preferable.

$R^5$, $R^6$, $R^7$ and $R^8$ are ones selected from a hydrogen, $C_1$-$C_{10}$ alkyl, $C_1$-$C_{10}$ halogenated alkyl, $C_6$-$C_{20}$ aryl, or $C_6$-$C_{20}$ halogenated aryl. These alkyls and aryls may have substituents and hetero atoms in their structures. $R^5$, $R^6$, $R^7$ and $R^8$ existing in a plural number may bond to each other through single bond or multiple bond to form a ring.

The constants h, i, j and k relating to the number of the ligands explained hereinbefore depend on the type of M of the center. It is preferable that h is 1 to 5, i is 0 to 2, j is 0 to 5, and k is 0 or 1.

In the following, specific examples of this complex are shown.

[Chemical Formula 2]

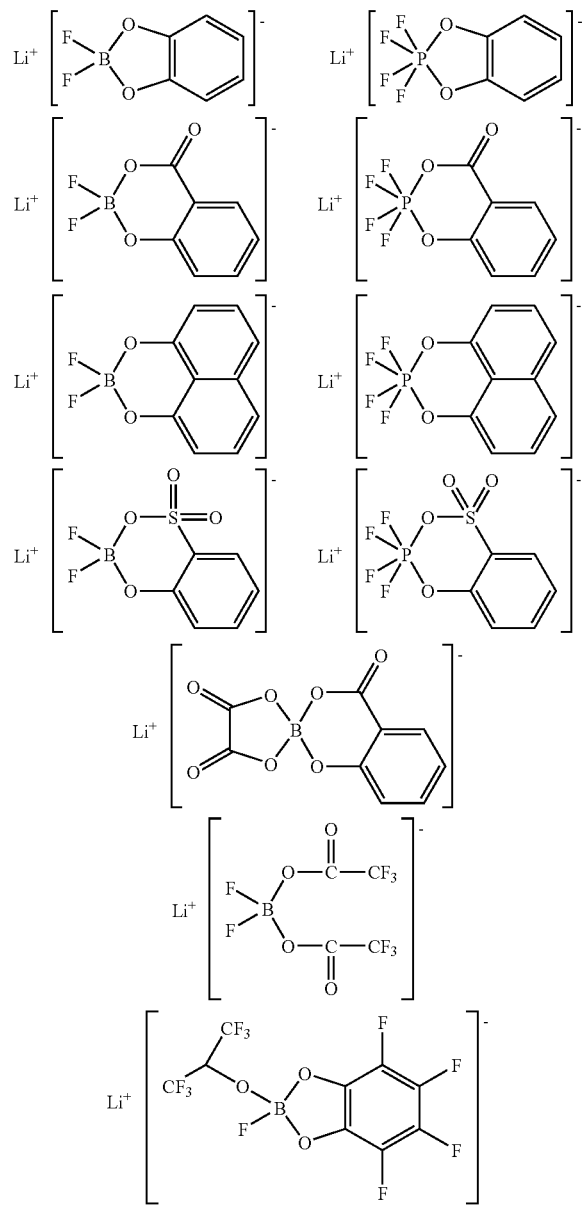

The method of the present invention for synthesizing the above complexes is explained. This method is characterized in that a ligand and a halogen-containing compound that becomes a supply source of the central element of the complex are reacted as raw materials in organic solvent in the presence of reaction aid.

The ligand is preferably one having an active hydrogen, alkali metal or alkali earth metal in order to bond to the halogen possessed by the halogen-containing compound, which becomes a supply source of the central element, and to eliminate it. Specifically, it is possible to mention alcohols, their metal alkoxides, carboxylic acids, their carboxylates, sulfonic acids, their sulfonates, sulfinic acids, their sulfinates, and the like. More preferably, this compound is a compound having a structure shown by the formula (2) or formula (3).

In the formulas (2) and (3), the symbols other than $E^1$, $E^2$ and $E^3$ are the same as those of the formula (1).

Next, the halogen-containing compound, which becomes a supply source of the central element, has a transition metal or group 13, group 14 or group 15 of the periodic table as the central element. It is one in which at least one halogen is bonded to this central element. It may be one in which only halogen is bonded, or one in which other substituents are also bonded. Preferably, this halogen-containing compound is a compound having a structure shown by the formula (4) or formula (5).

In the formulas (4) and (5), the symbols other than $R^9$ are the same as those of the formula (1). Herein, $R^9$ represents a halogen, preferably a fluorine. As specific examples, it is possible to mention $LiPF_6$, $LiBF_4$, $LiAlCl_4$, $LiPF_3(CF_3)_3$, $LiBF_3(Ph)$, $BF_3$, $PF_5$, and the like. Ph represents a phenyl group.

In the present invention, the reaction aid is a compound containing a group 1, group 2, group 13 or group 14 element of the periodic table. Preferably, it is a compound containing Al, B, Si, alkali metal or alkali earth metal. A strong bond between these elements and the halogen aids in the progress of the target reaction in the present invention. Specifically, it is one selected from chlorides, bromides, iodides, alkoxy compounds and carboxy compounds of the above-mentioned elements. More preferably, it is one selected from $AlCl_3$, $BCl_3$, and $SiCl_4$. $E^1R^9$, $E^2R^9$ or $E^3R^9$, which is generated in a small amount when the compound of the formula (2) or formula (3) and the compound of the formula (4) or the formula (5) have been mixed together, is removed by utilizing the reaction using this reaction aid. With this, the equilibrium shift in the direction of the target complex, resulting in the progress of the target reaction. It is desirable to select the ligand, the halogen-containing compound, and the reaction aid such that by-products are easily removed outside of the system as a precipitate or high-vapor-pressure component.

The quantitative ratio for conducting the reaction is not particularly limited. The ligand is reacted by 1 to 8 moles relative to 1 mole of the halogen-containing compound that becomes a supply source of the central element. The reaction aid is reacted by 0.1 to 10 times moles of the halogen-containing compound that becomes a supply source of the central element.

Although solvent used in the above-mentioned synthesis method depends on the structure of the compound, it is suitable to use one that dissolves even an extremely small amount of the compounds that become the raw materials and that does not react with the compounds in the system. It is preferably one having a relative dielectric constant of 2 or greater. Herein, in the case of using a solvent that has no dissolving power at all, the reaction becomes very slow. Therefore, it is not preferable. As long as it has even a slight solubility, the reaction proceeds rapidly since the target ionic complex has a high solubility. For example, it is possible to use carbonates, esters, ethers, lactones, nitrites, amides, sulfones, alcohols, aromatics, and the like. Besides a single solvent, it may be a mixed solvent of at least two kinds.

As specific examples of the solvent, it is possible to mention propylene carbonate, ethylene carbonate, diethyl carbonate, dimethyl carbonate, ethyl methyl carbonate, dimethoxyethane, acetonitrile, propionitrile, tetrahydrofuran, 2-methyltetrahydrofuran, dioxane, nitromethane, N,N-dimethylformamide, dimethylsulfoxide, sulfolane, γ-butyrolactone, toluene, ethanol, methanol, and the like.

Regarding the reaction temperature, −80° C. to 100° C., preferably 0° C. to 80° C., is used. If the temperature is lower than −80° C., the reaction may not proceed sufficiently. If the temperature is higher than 100° C., the solvent and the raw materials may be decomposed. The range of 0° C. to 80° C. is optimum in order to get a sufficient reaction rate and to generate no decomposition.

Since many of the raw materials used in the present invention have a hydrolytic property, it is desirable to conduct the synthesis in an atmosphere of a low-water-content air, nitrogen, argon, or the like.

It is also possible to purify the ionic complex, which has been obtained by the above-mentioned method, by a recrystallization method in which the solution is concentrated to precipitate crystals or a reprecipitation method in which a large amount of a poor solvent is added to the solution to precipitate them, followed by a method in which the obtained solid matter is washed, and the like.

In the following, the present invention is specifically explained by examples, but the present invention is not limited by such examples.

EXAMPLE 1

In a glove box of a dew point of −60° C., there were mixed together and dissolved 2.10 g of catechol, 1.90 g of lithium tetrafluoroborate (LiBF$_4$), and 8 mL of ethyl methyl carbonate. Next, 1.60 g of silicon tetrachloride as the reaction aid were slowly added to this mixed liquid at room temperature with stirring. Concurrently with the start of the addition, gas was generated vigorously. After termination of the addition, stirring was continued for 2 hr. The obtained reaction liquid was subjected to 45° C. and a reduced pressure condition of 133 Pa to remove ethyl methyl carbonate. With this, 2.60 g (yield: 83%) of lithium difluoro(catecholato)borate were obtained.

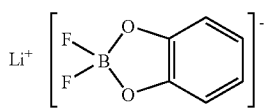

[Chemical Formula 3]

EXAMPLE 2

In a glove box of a dew point of −60° C., there were mixed together and dissolved 5.52 g of salicylic acid, 6.08 g of lithium hexafluorophosphate (LiPF$_6$), and 100 mL of diethyl carbonate. Next, 3.40 g of silicon tetrachloride as the reaction aid were slowly added to this mixed liquid at room temperature with stirring. Concurrently with the start of the addition, gas was generated vigorously. After termination of the addition, stirring was continued for 2 hr. The obtained reaction liquid was subjected to 45° C. and a reduced pressure condition of 133 Pa to remove diethyl carbonate. With this, 9.70 g (yield: 97%) of lithium tetrafluoro(salicylato)phosphate were obtained.

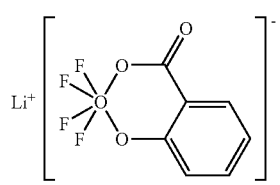

[Chemical Formula 4]

EXAMPLE 3

In a glove box of a dew point of −60° C., there were mixed together and dissolved 3.02 g of trifluoroacetic acid, 3.34 g of lithium tetrafluoroborate (LiBF$_4$), and 100 mL of diethyl carbonate. Next, 3.02 g of silicon tetrachloride as the reaction aid were slowly added to this mixed liquid at room temperature with stirring. Concurrently with the start of the addition, gas was generated vigorously. After termination of the addition, stirring was continued for 2 hr. The obtained reaction liquid was subjected to 45° C. and a reduced pressure condition of 133 Pa to remove diethyl carbonate. With this, 9.80 g (yield: 98%) of lithium difluorobis(acetoxy)borate were obtained.

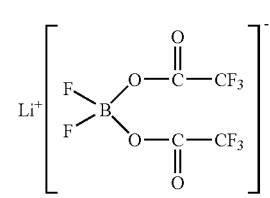

[Chemical Formula 5]

EXAMPLE 4

In a glove box of a dew point of −60° C., there were mixed together and dissolved 6.72 g of catechol, 1.91 g of lithium tetrafluoroborate (LiBF$_4$), 1.05 g of lithium fluoride, and 100 mL of diethyl carbonate. Next, 4.76 g of boron trichloride (BCl$_3$) as the reaction aid were slowly added to this mixed liquid at room temperature with stirring. Concurrently with the start of the addition, gas was generated vigorously. After termination of the addition, stirring was continued for 2 hr. The obtained reaction liquid was subjected to 45° C. and a reduced pressure condition of 133 Pa to remove diethyl carbonate. With this, 9.49 g (yield: 95%) of lithium difluoro(catecholato)borate were obtained.

EXAMPLE 5

In a glove box of a dew point of −60° C., there were mixed together and dissolved 2.10 g of catechol, 2.10 g of sodium tetrafluoroborate (NaBF$_4$), and 10 mL of dimethyl carbonate. Next, 1.61 g of silicon tetrachloride as the reaction aid were slowly added to this mixed liquid at room temperature with stirring. Concurrently with the start of the addition, gas was generated vigorously. After termination of the addition, stirring was continued for 2 hr. The obtained reaction liquid was subjected to 45° C. and a reduced pressure condition of 133 Pa to remove dimethyl carbonate. With this, 3.30 g (yield: 96%) of sodium difluoro(catecholato)borate were obtained.

EXAMPLE 6

In a glove box of a dew point of −60° C., there were mixed together and dissolved 2.10 g of catechol, 3.51 g of potassium hexafluorophosphate ($KPF_6$), and 20 mL of diethyl carbonate. Next, 1.61 g of silicon tetrachloride as the reaction aid were slowly added to this mixed liquid at room temperature with stirring. Concurrently with the start of the addition, gas was generated vigorously. After termination of the addition, stirring was continued for 2 hr. The obtained reaction liquid was subjected to 45° C. and a reduced pressure condition of 133 Pa to remove diethyl carbonate. With this, 4.36 g (yield: 90%) of potassium tetrafluoro(catecholato)phosphate were obtained.

EXAMPLE 7

In a glove box of a dew point of −60° C., there were mixed together 2.10 g of catechol, 4.15 g of tetaethylammonium tetrafluoroborate (($C_2H_5)_4NBF_4$), and 10 mL of dimethyl carbonate, thereby making a suspension condition. Next, 1.61 g of silicon tetrachloride as the reaction aid were slowly added to this mixed liquid at room temperature with stirring. Concurrently with the start of the addition, gas was generated vigorously, and the suspension gradually became clear. After termination of the addition, stirring was continued for 2 hr. The obtained reaction liquid was subjected to 45° C. and a reduced pressure condition of 133 Pa to remove dimethyl carbonate. With this, 5.32 g (yield: 97%) of tetaethylammonium difluoro(catecholato)borate were obtained.

What is claimed is:

1. A method for synthesizing an ionic metal complex having a chemical structural formula represented by the formula (1), comprising reacting at least one of a compound represented by the formula (2) and a compound represented by the formula (3) with a halogen-containing compound represented by the formula (4) or formula (5), in an organic solvent, in the presence of a compound containing an element of group 1, group 2, group 13 or group 14 of the periodic table as a reaction aid,

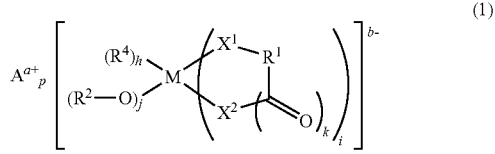

(1)

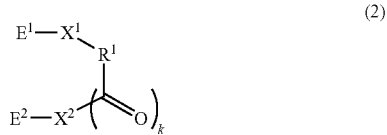

(2)

(3)

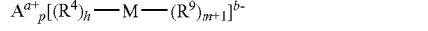

(4)

(5)

wherein M represents a transition metal or an element of group 13, group 14 or group 15 of the periodic table, $A^{a+}$ represents a metal ion, hydrogen ion, or onium ion, a represents 1-3, b represents 1-3, p represents b/a, h represents 1-5, i represents 0-2, j represents 0-5, k represents 0 or 1, m represents 0-4, the total of h, i and j is 3-6, at least one of i and j must necessarily be 1 or greater, $R^1$ represents a $C_3$-$C_{10}$ cycloalkylene, $C_3$-$C_{10}$ halogenated cycloalkylene, $C_6$-$C_{20}$ arylene, or $C_6$-$C_{20}$ halogenated arylene, wherein these alkylenes and arylenes may have substituents and hetero atoms in their structures, and $R^1$ existing by a number of i may bond to each other, $R^2$ represents a $C_1$-$C_{10}$ alkyl, $C_1$-$C_{10}$ halogenated alkyl, $C_6$-$C_{20}$ aryl, $C_6$-$C_{20}$ halogenated aryl, or —C(=O)$R^3$, wherein these alkyls and aryls may have substituents and hetero atoms in their structures, and $R^2$ existing by a number of j may bond to adjacent molecules to be in a polymer form, $R^3$ represents a halogen, $C_1$-$C_{10}$ alkyl, $C_1$-$C_{10}$ halogenated alkyl, $C_6$-$C_{20}$ aryl, or $C_6$-$C_{20}$ halogenated aryl, wherein these alkyls and aryls may have substituents and hetero atoms in their structures, and $R^3$ existing by a number of j may bond to adjacent molecules to be in a polymer form, $R^4$ represents a halogen, $C_1$-$C_{10}$ alkyl, $C_1$-$C_{10}$ halogenated alkyl, $C_6$-$C_{20}$ aryl, $C_6$-$C_{20}$ halogenated aryl, or $X^3R^5$, wherein these alkyls and aryls may have substituents and hetero atoms in their structures, and $R^4$ existing by a number of h may bond to each other to form a ring or may bond to adjacent molecules to be in a polymer form, $X^1$ represents O, S, $SO_3$, or $NR^6$; $X^2$ represents O, S, or $NR^7$; $X^3$ represents O, S, $SO_3$, $CO_2$, or $NR^8$, each of $R^5$, $R^6$, $R^7$ and $R^8$ independently represents a hydrogen, $C_1$-$C_{10}$ alkyl, $C_1$-$C_{10}$ halogenated alkyl, $C_6$-$C_{20}$ aryl, or $C_6$-$C_{20}$ halogenated aryl, wherein these alkyls and aryls may have substituents and hetero atoms in their structures, and $R^5$, $R^6$, $R^7$ and $R^8$ existing in a plural number may bond to each other through single bond or multiple bond to form a ring or may bond to adjacent molecules to be in a polymer form, each of $E^1$, $E^2$ and $E^3$ independently represents a hydrogen or alkali metal, and $R^9$ represents a halogen;

wherein if i represents 1 or 2, then the ring defined by M, $X^1$, $R^1$, (C=O)$_k$ and $X^2$ in formula (1) is a five-membered or six-membered chelate ring; wherein M is Al, B, V, Ti, Si, Zr, Ge, Sn, Cu, Y, Zn, Ga, Nb, Ta, Bi, P, As, Sc, Hf, or Sb.

2. A method for synthesizing an ionic complex according to claim 1, which is characterized in that the reaction aid is a compound of Al, B, Si, alkali metal or alkali earth metal.

3. A method for synthesizing an ionic complex according to claim 1, which is characterized in that the reaction aid is a chloride, bromide, iodide, alkoxy compound or carboxy compound of Al, B, Si, alkali metal or alkali earth metal.

4. A method for synthesizing an ionic complex according to claim 1, which is characterized in that the reaction aid is $AlCl_3$, $BCl_3$, or $SiCl_4$.

5. A method for synthesizing an ionic complex according to claim 1, which is characterized in that $A^{a+}$ is a lithium ion, sodium ion, potassium ion, hydrogen ion, or quaternary alkylammonium ion.

6. A method for synthesizing an ionic complex according to claim 1, which is characterized in that $R^9$ is a fluorine.

* * * * *